(12) United States Patent
Tomasso et al.

(10) Patent No.: US 7,597,847 B2
(45) Date of Patent: Oct. 6, 2009

(54) ANALYZER HAVING A STATIONARY MULTIFUNCTION PROBE

(75) Inventors: David Angelo Tomasso, Rochester, NY (US); Raymond Francis Jakubowicz, Rush, NY (US); James Vanselow Barry, Rochester, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 574 days.

(21) Appl. No.: 10/403,266

(22) Filed: Mar. 31, 2003

(65) Prior Publication Data

US 2004/0191121 A1   Sep. 30, 2004

(51) Int. Cl.
*G01N 9/30*   (2006.01)
(52) U.S. Cl. .............................. 422/64; 436/45; 422/72
(58) Field of Classification Search ................. 422/104, 422/64, 72; 436/43, 44, 45
See application file for complete search history.

(56) References Cited

U.S. PATENT DOCUMENTS

| | | | |
|---|---|---|---|
| 3,826,622 | A | 7/1974 | Natelson |
| 4,086,060 | A | 4/1978 | Hermann, Jr. |
| 4,142,863 | A | 3/1979 | Covington et al. |
| 4,269,803 | A | 5/1981 | Jessop |
| 4,287,155 | A | 9/1981 | Tersteeg et al. |
| 4,296,070 | A | 10/1981 | Montalto et al. |
| 4,347,750 | A | 9/1982 | Tersteeg et al. |
| 4,458,812 | A | 7/1984 | Dreier et al. |
| 4,512,952 | A | 4/1985 | Blanding et al. |
| 4,797,257 | A | 1/1989 | Shaw |
| 4,815,978 | A | 3/1989 | Mazza et al. |

(Continued)

FOREIGN PATENT DOCUMENTS

EP       0388018       9/1990

(Continued)

OTHER PUBLICATIONS http://www.abaxisinc.com/_vet/vhem.html—Abaxis.com, VetScan® Chemistry System, Sep. 18, 2002, 2 pgs.

(Continued)

*Primary Examiner*—Jill Warden
*Assistant Examiner*—Natalia Levkovich
(74) *Attorney, Agent, or Firm*—Todd J Burns

(57) ABSTRACT

An analyzer, preferably a desktop analyzer, includes: a stationary probe capable of dispensing or aspirating a liquid; one or more of a movable test element or movable liquid source; and a conveyor for moving the movable test element or liquid source with respect to the stationary probe. In a preferred embodiment, the conveyor includes a dual rotor conveyor. A method of dispensing or aspirating a liquid into a test element includes: providing a movable test element having identifying marks, such as a barcode, thereon and a movable sample liquid supply; providing a stationary probe; reading the identifying marks to determine which test is to be performed and the dimensions of the test element; moving the movable sample liquid supply into registration with the probe; aspirating sample into the stationary probe; and moving the movable test element into registration with the probe, wherein the registration of the test element with the probe is controlled by the test to be performed. In a preferred embodiment, the method is implemented by a computer program interfacing with a computer.

22 Claims, 5 Drawing Sheets

U.S. PATENT DOCUMENTS

| | | | |
|---|---|---|---|
| 4,933,291 A | 6/1990 | Daiss et al. | |
| 4,965,049 A | 10/1990 | Lillig et al. | |
| 5,059,393 A | 10/1991 | Quenin et al. | |
| 5,089,418 A | 2/1992 | Shaw et al. | |
| 5,102,624 A | 4/1992 | Muraishi | |
| 5,204,269 A * | 4/1993 | Barker et al. | 436/47 |
| 5,219,526 A | 6/1993 | Long | |
| 5,244,633 A | 9/1993 | Jakubowicz et al. | |
| 5,314,825 A | 5/1994 | Weyrauch et al. | |
| 5,326,398 A | 7/1994 | Kelley et al. | |
| 5,346,672 A | 9/1994 | Stapleton et al. | |
| 5,428,470 A | 6/1995 | Labriola, II | |
| 5,441,895 A | 8/1995 | Jakubowicz et al. | |
| 5,480,484 A | 1/1996 | Kelley et al. | |
| 5,523,056 A | 6/1996 | Miller | |
| 5,525,298 A | 6/1996 | Anami | |
| 5,736,403 A | 4/1998 | Riall et al. | |
| 5,741,708 A | 4/1998 | Carey et al. | |
| 5,747,666 A | 5/1998 | Willis | |
| 5,753,512 A | 5/1998 | Riall et al. | |
| 5,787,015 A | 7/1998 | Aldridge et al. | |
| 5,885,533 A | 3/1999 | Savage et al. | |
| 5,965,447 A | 10/1999 | Sekiyama et al. | |
| 5,968,329 A | 10/1999 | Anderson et al. | |
| 5,980,830 A | 11/1999 | Savage et al. | |
| 5,983,734 A | 11/1999 | Mathur et al. | |
| 6,013,528 A | 1/2000 | Jacobs et al. | |
| 6,190,617 B1 * | 2/2001 | Clark et al. | 422/104 |
| 2001/0019842 A1 | 9/2001 | Kitamura et al. | |
| 2002/0098116 A1 | 7/2002 | Sugaya et al. | |
| 2002/0106308 A1 | 8/2002 | Zweifel et al. | |
| 2003/0017613 A1 | 1/2003 | Jakubowicz et al. | |
| 2004/0121484 A1 | 6/2004 | Betancourt et al. | |
| 2004/0191923 A1 | 9/2004 | Tomasso et al. | |
| 2005/0123444 A1 | 6/2005 | Tomasso et al. | |

FOREIGN PATENT DOCUMENTS

| | | | |
|---|---|---|---|
| EP | | 458138 A2 | 11/1991 |
| EP | 0 513 618 A2 | | 11/1992 |
| EP | | 0571035 | 11/1993 |
| EP | | 0388018 B1 | 8/1995 |
| EP | | 0722089 B1 | 10/1998 |
| EP | | 747 708 B1 | 8/2002 |
| EP | | 0747708 | 8/2002 |
| EP | | 1464963 A2 | 10/2004 |
| WO | WO 97/41445 A1 | | 11/1997 |
| WO | WO 02/081088 | | 10/2002 |

OTHER PUBLICATIONS http://www.hemagen.com/Products/analyst.htm—Analyst® benchtop chemistry system, System Features , Sep. 18, 2002, 2 pgs.

Search—Nerac.com—Jan. 20, 2003—Question No. 1186511.004, 1. NDN 223-0119-8869-0: *Biochemical analysis system, and biochemical analysis element cartridge* US Pub. No. 20020098116A1.

Search—Nerac.com—Jan. 20, 2003—Question No. 1186511.004, 2. NDN 223-0118-3060-7: *Incubator* US Pub. No. 20020090322 A1.

Search—Nerac.com—Jan. 20, 2003—Question No. 1186511.004, 3. NDN 223-0118-3058-9 *Incubator* US Pub. No. 20020090321 A1.

Search—Nerac.com—Jan. 20, 2003—Question No. 1186511.004, 4. NDN 223-0107-5493-2: *Quantitative suction tip and quantitative suction apparatus* US Pub. No. 20020037239 A1.

Search—Nerac.com—Jan. 20, 2003—Question No. 1186511.004, 5. NDN 223-0106-4499-3: *Biochemical analysis apparatus* US Pub. No. 20020031844A1.

Search—Nerac.com—Jan. 20, 2003—Question No. 1186511.004, 6. NDN 223-0008-3503-0; *Analysis method using dry chemical analysis element* US Pub. No. 20010041367 A1.

Search—Nerac.com—Jan. 20, 2003—Question No. 1186511.004, 7. NDN 050-0062-9931-3: Chemical analysis system EPO Pub. No. 0932043.

Search—Nerac.com—Jan. 20, 2003—Question No. 1186511.004, 8. NDN 050-0062-9930-1, Chemical analysis system and blood filtering unit—EPO Pub. No. 0932042.

Search—Nerac.com—Jan. 20, 2003—Question No. 1186511.004, 9. NDN 050-0060-7344-0, Method of filtering blood—EPO Pub. No. 0893130.

Search—Nerac.com—Jan. 20, 2003—Question No. 1186511.004, 10. NDN 050-0054-2680-7, Blood filter unit—EPO Pub. No. 0785012.

Search—Nerac.com—Jan. 20, 2003—Question No. 1186511.004, 11. NDN 050-0049-5101-3, Chemical analysis film cartridge and method of and device for taking out chemical analysis film chip from the cartridge, EPO Pub. No. 0722089.

Search—Nerac.com—Jan. 20, 2003—Question No. 1186511.004, 12. NDN 050-0047-3882-2, Method and apparatus for spotting liquid samples onto dry-type chemical analysis film pieces, EPO Pub. No. 0677744.

Search—Nerac.com—Jan. 20, 2003—Question No. 1186511.004, 13. NDN 050-0044-8620-1, Chemical analysis film cartrige and method of and device for taking out chemical analysis film from the cartridge, EPO Pub. No. 0634659.

Search—Nerac.com—Jan. 20, 2003—Question No. 1186511.004, 14. NDN 050-0039-6047-0, Chemical analysis system, EPO Pub. No. 0555654.

Search—Nerac.com—Jan. 20, 2003—Question No. 1186511.004, 15. NDN 050-0028-3318-9, Film loading device, EPO Pub. No. 0415425.

Search—Nerac.com—Jan. 20, 2003—Question No. 1186511.004, 16. NDN 050-0017-5714-3, Automatic analytical method using chemical analytical slides, EPO Pub. No. 0285851.

Search—Nerac.com—Jan. 20, 2003—Question No. 1186511.004, 17. NDN 069-0341-4631-5, Chemical analysis stem, EPO Pat. No. 0555654.

Search—Nerac.com—Jan. 20, 2003—Question No. 1186511.004, 18. NDN 069-0338-2933-2, Method and apparatus for spotting liquid samples onto dry-type chemical analysis film pieces, EPO Pat. No. 0677744.

Search—Nerac.com—Jan. 20, 2003—Question No. 1186511.004, 19. NDN 069-327-5321-6, Method of and device for taking out chemical analysis film test elements from a cartridge, EPO Pat. No. 0722089.

Search—Nerac.com—Jan. 20, 2003—Question No. 1186511.004, 20. NDN 069-0322-6328-6, Chemical analysis film cartridge and method of taking out chemical analysis film test elements from the cartridge, EPO Pat. No. 0634659.

Search—Nerac.com—Jan. 20, 2003—Question No. 1186511.004, 21. NDN 069-0317-3206-0, Film loading device, EPO Pat. No. 0415425.

Search—Nerac.com—Jan. 20, 2003—Question No. 1186511.004, 22. NDN 069-0303-0232-0, Automatic analytical method using chemical analytical slides, EPO Pat. No. 0285851.

Search—Nerac.com—Jan. 20, 2003—Question No. 1186511.004, 23. NDN 043-0254-5389-8, Pipette Chip Loading Implement, Citation from Patent Abstracts of Japan No. 02207047 JP.

Search—Nerac.com—Jan. 20, 2003—Question No. 1186511.004, 24. NDN 043-0254-5388-6, Incubator, Citation from Patent Abstracts of Japan No. 02207046 JP.

Search—Nerac.com—Jan. 20, 2003—Question No. 1186511.004, 25. NDN 043-0254-5387-4, Incubator, Citation from Patent Abstracts of Japan No. 02207045 JP.

Search—Nerac.com—Jan. 20, 2003—Question No. 1186511.004, 26. NDN 043-0254-5386-2, Incubator Device, Citation from Patent Abstracts of Japan No. 02207044 JP.

Search—Nerac.com—Jan. 20, 2003—Question No. 1186511.004, 27. NDN 043-0252-0179-4, Cartridge for Biochemical Analysis, Citation from Patent Abstracts of Japan No. 02181834 JP.

Search—Nerac.com—Jan. 20, 2003—Question No. 1186511.004, 28. NDN 043-0252-0178-2, Biochemical Analyzer, Citation from Patent Abstracts of Japan No. 02181833 JP.

Search—Nerac.com—Jan. 20, 2003—Question No. 1186511.004, 29. NDN 043-0252-0177-0, Cartridge for Biochemical Analysis, Citation from Patent Abstracts of Japan No. 02181832 JP.

Search—Nerac.com—Jan. 20, 2003—Question No. 1186511.004, 30. NDN 043-0243-7088-2, Method and Device for Detecting Spot of Liquid, Citation from Patent Abstracts of Japan No. 02098707 JP.

Search—Nerac.com—Jan. 20, 2003—Question No. 1186511.004, 31. NDN 043-0243-7087-0, Quantitative Suction Tip and Quantitative Suction Device, Citation from Patent Abstracts of Japan No. 02098706 JP.

Search—Nerac.com—Jan. 20, 2003—Question No. 1186511.004, 32. NDN 043-0242-8766-8, Biochemical Analyzer, Citation from Patent Abstracts of Japan No. 02090377 JP.

Search—Nerac.com—Jan. 20, 2003—Question No. 1186511.004, 33. NDN 217-0406-9896-3, Chemical analysis system and blood filtering unit—U.S. Patent No. 6,241,947.

Search—Nerac.com—Jan. 20, 2003—Question No. 1186511.004, 34. NDN 217-0391-7176-6, Blood Filter Unit, U.S. Patent No. 6,170,671.

Search—Nerac.com—Jan. 20, 2003—Question No. 1186511.004, 35. NDN 217-0364-4367-6, Method of Filtering Blood U.S. Patent No. 6,170,671.

U.S. Appl. No. 10/403,153, Tomasso, et al.

U.S. Appl. No. 10/730,749, Tomasso, et al.

U.S. Appl. No. 10/436,537, Tomasso, et al.

European Search Report, dated Dec. 17, 2004, for European Appln. No. EP 0425 1924.

* cited by examiner

ANALYZER HAVING A STATIONARY MULTIFUNCTION PROBE

BACKGROUND OF THE INVENTION

1. Field of the Invention

The present invention relates to a stationary probe for an analyzer. In particular, the present invention relates to a desktop analyzer having a stationary probe for aspirating or dispensing a liquid.

2. Description of the Related Art

Desktop analyzers, particularly for veterinary use and point of care (POC) human use, are known in the art. For example, the Abaxis Vetscan™ and Hemagen Analyst™ are both desktop analyzers for veterinary use. The Vitros DT-60™ is a desktop analyzer manufactured by Ortho-Clinical Diagnostics Corp. Other known analyzers include those POC analyzers described in U.S. Pat. Nos. 5,968,329, 5,747,666, 5,980,830, and 5,787,015, all of which are incorporated by reference in their entireties. U.S. Pat. No. 4,965,049 also discloses a modular analyzer system. U.S. Pat. No. 5,983,734 discloses a modular automated diagnostic system. U.S. Patent Application Publication No. 2002/0098116 ('116 publication) describes a biochemical analysis system. U.S. Pat. No. 4,797,257 describes analyzers and their components that use slides as test elements. U.S. Pat. No. 5,314,825 discloses a chemical analyzer having a rotary cuvette holder and a pivoting probe. These publications are also incorporated by reference in their entireties.

Known diagnostic systems, such as those described above, have generally adequately addressed size issues but often at the expense of functionality, test menu, and productivity. Most known systems perform tests serially on a single patient sample, significantly limiting walk away time for the user to perform other work tasks. These analyzers usually employ a number of dedicated subsystems within the analyzer to perform discrete functions such as sample storage and positioning, reagent storage, and waste collection among others. In some cases, multiple analyzer systems are required to perform the variety of test menus needed in the lab, for example, separate systems to perform immuno rate or electrolyte assays.

In many known systems, whole blood samples must be prepared (e.g., diluted or centrifuged) prior to testing, further limiting the users productivity. Reagent formats can be individual test strips (e.g., such as dry-slide technology), which offer the most cost effective solution and test flexibility, or multiple test formats (e.g., such as the Abaxis Vetscan™ rotor), which limit selective assay testing, and, as a result, drive up test costs. Liquid systems may compromise analytical performance when dealing with patient sample background interference compared to analyzers that use a dry-slide format. However, there are some tests which are incompatible with dry formats and therefore must use wet or liquid formats.

There is a need for small, portable in vitro diagnostic systems that are capable of automatically performing a wide range of analysis, preferably for both human and animal health care providers, and provide the flexibility to execute a variety of operations on patient samples with a high degree of simplicity and cost effectiveness. There are a number of factors that drive the need for improved products including:

Cost Pressures—Lower cost testing solutions that more effectively utilize system reagents and operation.

Ease of Use—Users at the POC and veterinary labs are often less skilled than most technicians working in large lab operations and often perform a wide range of lab and office functions. Systems utilized in these labs must be simple to use but offer a high degree of functionality. Systems that are easy to use with little maintenance or preparation of both sample and instrument are advantageous.

Increased Test Menu Capability—Systems are needed that can perform a wide range of tests without compromising analytical performance due to test format limitations. Current systems penalize the user due to their inflexibility to accommodate individual and panel tests without additional reagent waste associated with pre-configured test formats (e.g., the Abaxis Vetscan™ rotor or the Hemagen Analyst™ Panels+ test rotor).

Size—Lab space is often very limited and portability is often a factor allowing the analyzer to be used at the patient location.

In developing such systems that achieve the above factors, there is a need to minimize the number of moving parts to save on costs and minimize space requirements. Known analyzers often use moving probes (e.g., U.S. Pat. Nos. 4,965,049 and 6,013,528 and the '116 publication) to align the probe with the test element, such as a well or slide, in order to dispense or aspirate the fluid being analyzed or assayed. Moving probes can also be used to aspirate and dispense diluent, reagent, wash and reference fluids. In some instances, the probes must be aligned precisely with the target receptacle. This results in expensive and space consuming motors, transmissions and control systems.

SUMMARY OF THE INVENTION

One object of the invention is to overcome the disadvantages of the known art described above. Another object of the invention is to provide a desktop analyzer that can perform an array of different analysis within a compact space. Another object of the invention is to provide a stationary multifunction probe for an analyzer. Yet another object of the invention is to provide a method of dispensing or aspirating a fluid into a test element that includes using a stationary probe. Yet another object of the invention is to provide a method of analyzing a sample.

The foregoing and further objects of the invention are accomplished according to one aspect of the invention that provides an analyzer that includes: a stationary probe capable of dispensing or aspirating a liquid; one or more of a movable test element or movable liquid source; and a conveyor for moving the movable test element or liquid source with respect to the stationary probe. In a preferred embodiment, the conveyor includes a dual rotor conveyor. In another preferred embodiment, the analyzer is a desktop analyzer.

According to another aspect of the invention, there has been provided a method of dispensing or aspirating a liquid into and/or onto a test element that includes: providing a movable test element having identifying marks, such as a barcode, thereon and a movable sample liquid supply; providing a stationary probe; reading the identifying marks to determine which test is to be performed and optionally the dimensions of the test element; moving the movable sample liquid supply into registration with the probe; aspirating sample into the stationary probe; and moving the movable test element into registration with the probe, wherein the registration of the test element with the probe is controlled by the test to be performed. In a preferred embodiment, the method is implemented by a computer program interfacing with a computer.

According to another aspect of the invention, there has been provided an article of manufacture comprising a computer usable medium having computer readable program code configured to conduct the method described above.

Further objects, features and advantages of the present invention will be apparent to those skilled in the art from detailed consideration of the preferred embodiments that follow.

DETAILED DESCRIPTION OF PREFERRED EMBODIMENTS

Figure 1:
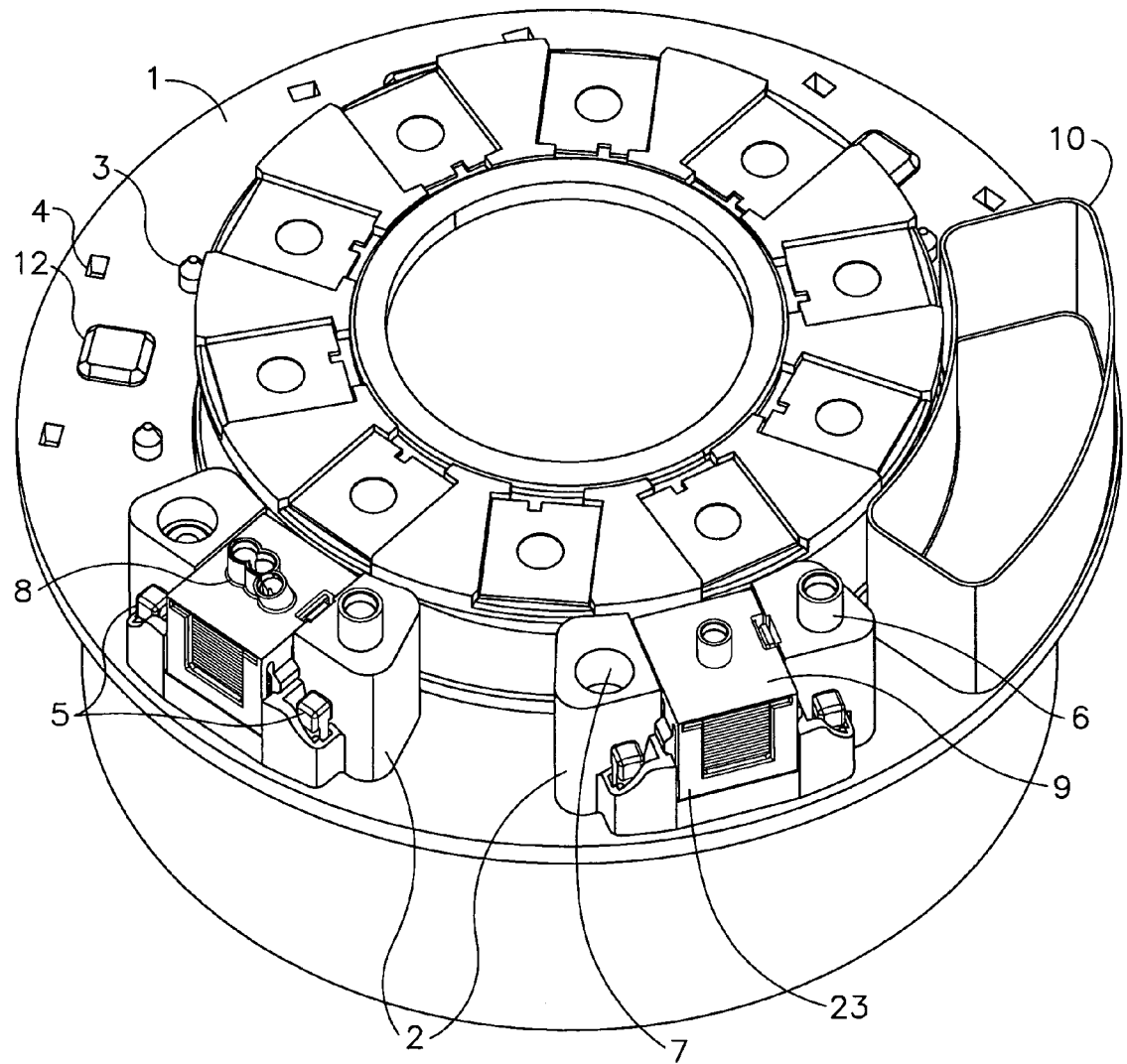
FIG. 1 shows a perspective view of a desktop analyzer according to one embodiment of the present invention.

The present invention is directed to an in vitro analyzer for use in human and animal diagnostics. The analyzer of the present invention allows for simplified panel testing, e.g., a "chem 7" or "chem 20" panel, with the option to add individual tests as required by the user without generating unnecessary reagent waste or unwanted tests. The device is simple to use and allows the user the opportunity to place multiple patient samples on the device that will automatically process the tests without further intervention by the user.

In order to make such a compact design possible, one aspect of the present invention provides an analyzer that includes a stationary fluid probe and movable test element(s) or movable fluid, preferably liquid, supply(ies). An important feature of the invention is the stationary probe. The stationary probe preferably is a probe, such as a nozzle capable of aspirating and/or dispensing a liquid, preferably in a metering fashion. As used herein, "stationary" is defined as the probe being stationary along at least one axis of an x, y and z coordinate system. Preferably, the probe is only movable along a single axis, such as the vertical "z" axis. Movement in the vertical direction allows the probe to access tips, samples, waste, etc., which may be at different heights. Thus, with the exception of vertical movement of the probe, all movement is confined to the movable test element, which in some embodiments is transported by a moving rotor. This has the significant advantage over typical known analyzers in that additional cost and complexity that would result from a probe transport system is avoided. That is, a simple control system in one dimension (in this case vertical) is all that is required for the stationary probe, as opposed to a more complex control system required for more degrees of freedom. Thus, instead of a complex transport and control systems as used in known analyzer probe transports (i.e., multiple servo motors and controllers being provided), a much simpler transport and control system is all that is required.

Preferably, the probe includes a probe or metering tip, preferably disposable, that actually contacts the fluid being manipulated. In one embodiment, an additional probe, such as a reference fluid dispensing nozzle, may also be provided. Due to space limitations, it may be desirable to have some movement of the additional probe, such as to move from a fluid source, e.g., a source of reference fluid, to the dispense position over the test element. In such an instance, the movement of the additional probe could be limited to movement in a straight line or a single plane, due to the position of one opening of the probe guide (described below), which would be located to receive the additional probe. This would simplify construction by dispensing with the requirement of providing motion and control systems for three dimensional movement.

In order to make such a compact design further possible, one embodiment of the present invention also provides a test element holder, such as a test element cartridge, that includes a guide for positioning a fluid probe, such as an aspirating or dispensing nozzle with a test element or fluid source being acted upon. Further details of the test element cartridge and a guide can be found in copending application entitled "Test Element Holder with a Probe Guide for an Analyzer"(Ser. No. 10/403,153) filed concurrently herewith and incorporated by reference in its entirety.

The test element can be a slide containing the reagents necessary for the analysis, the so-called dry-slide technology as described in U.S. Pat. No. 4,797,257 or a cup-shaped well as described in U.S. Pat. No. 5,441,895, which are incorporated by reference in their entireties. The test element can also be the so-called test strip chemistry.

Broadly, the test element holder contains test elements to be dispensed. Typically this would include multiple test elements, however, in some embodiments, such as wells for a wet analysis, it can be envisioned that a single test element may be employed. The holder can also be termed a cassette. The holder includes a body portion for holding at least one test element and a guide adapted to receive a probe to position the probe in a desired registration with the test element. Preferably, the test element holder includes a recess for holding the test elements and a cover for the test element or other fluid source being acted upon by the probe. Suitable cassettes are described in U.S. Pat. Nos. 4,142,863 and 4,512,952, both incorporated by reference in their entireties.

Located within the cover is at least one opening, preferably two and more preferably three openings adapted to receive the probe tip. The opening(s) can include a surface that extends away from the opening and at least partially surrounds the opening(s). Preferably, the openings are round and the surface has at least a partially cylindrical shape. The surface can open in an increasing manner in a direction away from the hole toward the probe tip to assist in guiding the probe into registration with the test element. For example, the surface can have the shape of a truncated cone.

Figure 2:
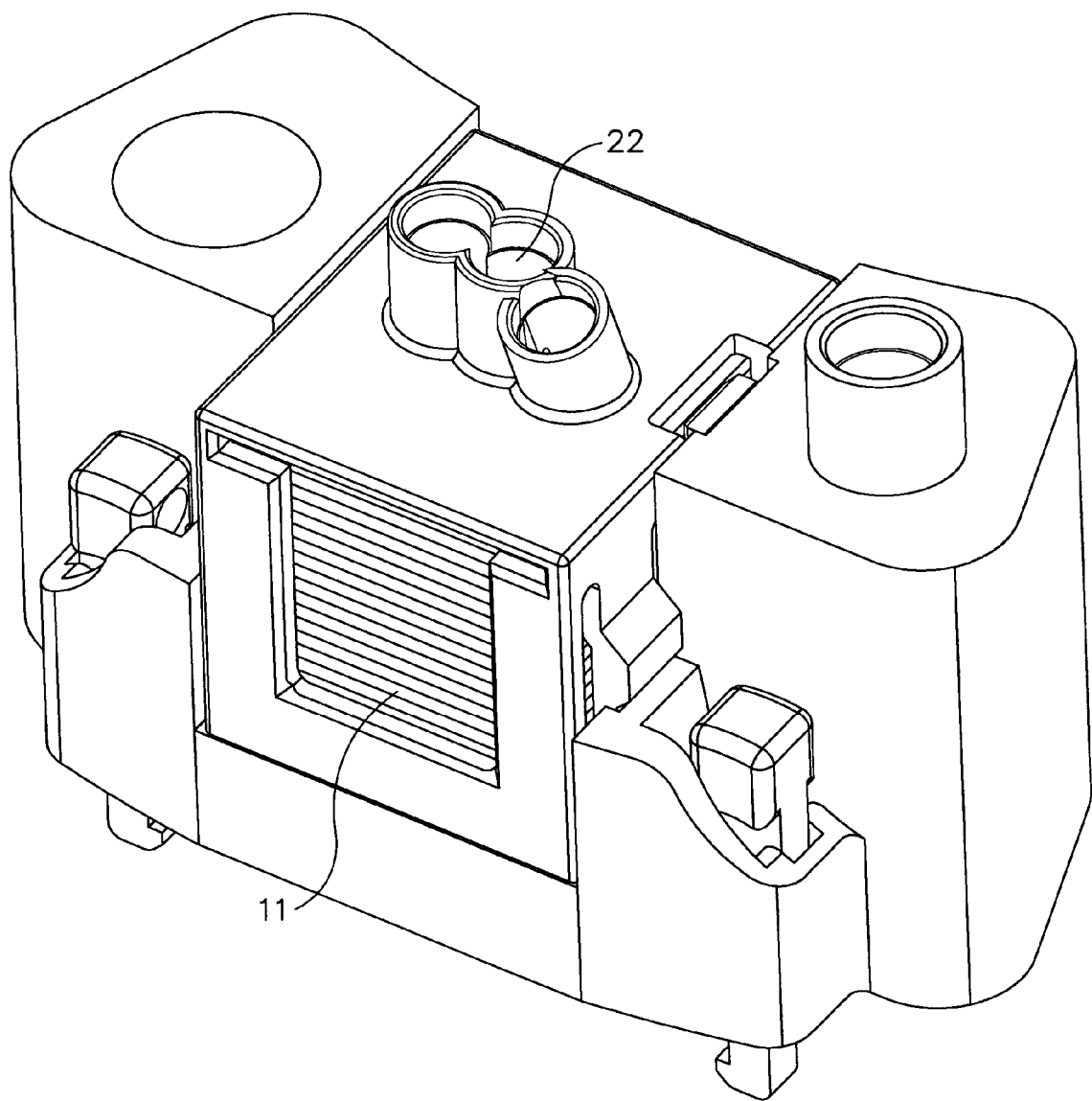
FIG. 2 shows a perspective view of a test element holder that includes a probe guide according to one embodiment of the present invention.

In one embodiment, there are a plurality of openings and one of the openings opens in a direction that is different than the other openings. This can be provided for a variety of reasons. For example, in some embodiments, there may be provided multiple probes, such as one for sample and the other for reference fluids for potentiometric analysis as described above, that are positioned at different angles with respect to the test element or other fluid sources. In this embodiment, the other opening can receive the probe in the same manner as the other opening that have an open perpendicular to the covering of the test element. It should be understood that the description of the plurality of holes above encompasses designs where the holes share common sectors with each other, such that there are no discontinuities between holes. That is, the holes overlap to a certain extent. This is illustrated in FIG. 2. This allows the probe tips to be positioned closer to each other than if the probe guide holes were completely separate. Exemplary probe guides can be found in U.S. Pat. No. 4,797,257, described above.

The probe guide can be an integral or unitary one-piece construction with the holder, or a separate attached structure. In a preferred embodiment, the guide alone or the integral guide and holder are formed from an injection molded plastic. In some embodiments, the test elements may come pre-packaged in a disposable test element holder. In these embodiments, the probe guide may likewise be disposable, preferably recyclable. Of course, if the probe guide is separately attachable to the test element holder, it can be independently disposable. At least periodic disposal is particularly advantageous, because it dispenses with cleaning requirements, reduces the likelihood of carryover between samples, and reduces tolerance buildup.

In a preferred embodiment, a movable fluid supply of the analyzer that can be removably attached to the desktop analyzer is provided in conjunction with the stationary probe. The test element holder with the probe guide can be included with, and preferably in, the movable fluid supply. In a preferred embodiment, the test element holder sits in a recess of the movable fluid supply. The movable fluid supply can also include a probe tip holder and a fluid supply section and is preferably of a one-piece construction. The probe tip holder retains a tip that will be used to aspirate the fluid in the fluid supply section. The fluid supply section contains the fluid, such as whole blood, serum plasma, wash fluid, or a diluent to be aspirated and dispensed onto the test element. These can also be recesses in the movable fluid supply. Thus, in one unit, all components of the analyzer that are required to be in registration with the probe tip can be included in the fluid supply section In another preferred embodiment of the invention, a plurality of test element holders with probe guides are provided. By providing a test element holder with a corresponding probe guide, different test elements, such as potentiometric and colorimetric test elements, or wet and dry test elements, can be used together on a single analyzer, providing a significant benefit in reducing size and providing optimum flexibility in analysis. Further details of multiple test element holders are described in copending application entitled "Test Element Holder with a Probe Guide for an Analyzer" filed concurrently herewith and incorporated by reference in its entirety.

Another embodiment of the present invention, which is significant in reducing size and providing optimum flexibility in analysis, involves the probe being stationary (as described above) and the test element(s) making all significant movements, such as by the rotors described below, to bring the test element and probe into the desired registration.

The materials of construction for the analyzer, including the probe guide, test element holder and movable fluid supply can include all suitable materials known in the art, such as plastic or metal. The disposable items of the analyzer, such as the test element holder and metering tips are preferably made from environmentally friendly, recyclable materials.

Another aspect of the invention provides a method of aspirating or dispensing a liquid, or more preferably performing an analysis on a sample, using the analyzer according to the present invention. In one preferred embodiment, the type of analysis or test to be performed on a sample is selected. Based on the test to be performed, one or more movable test elements, corresponding to the test to be performed, are loaded onto the analyzer, preferably in the movable liquid supply. The test elements preferably contain identification indicia or marks, such as a barcode, that can be read by the analyzer to determine the test to be performed and optionally the physical dimensions of the test element. In some instances the analysis to be performed is also inputted into the control system for the analyzer, preferably through a keyboard of a computer that controls the analyzer.

A sample is provided, preferably on the movable fluid supply. The movable fluid supply containing the sample and test elements is loaded onto the analyzer. Depending on the number and type of analysis to be performed, more than one movable fluid supply may be required. Upon activation of the analyzer, a transport system or conveyor moves the movable fluid supply into registration with the stationary probe. In some embodiments, a disposable probe tip is pre-loaded onto the movable fluid supply and the probe first receives the tip. The sample is then moved into registration with the probe and the probe aspirates sample into the tip. After aspirating the sample, the test elements are moved into registration with the probe. A pre-selected amount of the sample is dispensed from the probe tip onto or into the test element. If necessary, a supply of liquid reagent, such as horseradish peroxide oxidase ("HPO"), can be moved into registration with the stationary probe. The probe aspirates the reagent and retains the reagent until the sample has moved back into registration with the probe, at which point, the reagent is dispensed onto the test element containing the sample.

At this point, if incubation is required, the test element containing the sample, can be incubated. On those preferred embodiments that contain a dual-rotor configuration as described below, the test element can be transferred to the inner rotor and incubated, while the outer reagent rotor continues the function of transporting sample and test elements into registration with the stationary probe. After incubation, the sample can be optionally washed, once again, by moving a supply of liquid wash into registration with the stationary probe. After washing, the sample can be transferred to a spectrometer to have its signal read. On chemiluminscent applications where a signal reagent is needed, once again, a supply of signal reagent is moved into registration with the probe to be aspirated and then dispensed onto the washed sample. After completion of the analysis, the test element can be disposed of. In those embodiments that make use of an inner movable ring, the inner ring may be brought into registration with a waste container on the outer ring and ejected into the waste container. Likewise, the outer reagent rotor can rotate the waste container into alignment with the stationary probe and receive the used probe tip(s).

The present invention will now be illustrated in connection with the following detailed preferred embodiment. Of course, the preferred embodiment is intended for illustrative purposes only and is not intended to limit the scope of the invention.

In a preferred embodiment, the analyzer includes dual concentric rotors. Samples may be whole blood, which may be automatically centrifuged prior to metering, or a variety of other sample types including serum, plasma and urine, among others. The concentric rotors work in concert to process a wide variety of analytical tests with little intervention by the user.

The outer reagent rotor carries the movable fluid supply(ies) and eliminates the need for multiple system modules and associated complexity since it is capable of storing and processing samples, test elements, liquid reagents, disposables and waste on a single platform. The multifunctional outer reagent rotor allows the user to place multiple patient samples on the rotor in addition to individual, assay specific test slides in test cartridges. The movable fluid supply also accepts whole blood samples, which can be automatically centrifuged on the analyzer or prepared samples. The outer reagent rotor is also capable of positioning a variety of movable fluid supplies in various formats that allow for auto dilution of samples and expanded test menu capability through the addition of wash fluids for immuno rate assays. The reagent rotor is also capable of accepting a waste collection container to collect the various test slides and metering tips. The outer reagent rotor is automatically positioned to intersect a fixed metering system, that includes the fluid probe, used to aspirate and dispense various fluids.

The inner incubator rotor is used to incubate the slides at a predetermined temperature then position the slide for measurement by a sensitometry device, such as a reflectometer, electrometer or spectrometer. Test slides are then ejected from the incubator rotor into a common waste collection container placed on the reagent rotor. The waste collection container is also able to collect other test consumables such as disposable probe tips due to the random access positioning capability of the reagent rotor.

All test processing and waste collection is accomplished within the rotors. Additional system features not shown can include an integral printer, user interface keypad/display, electronics and cabinetry.

Figure 5:
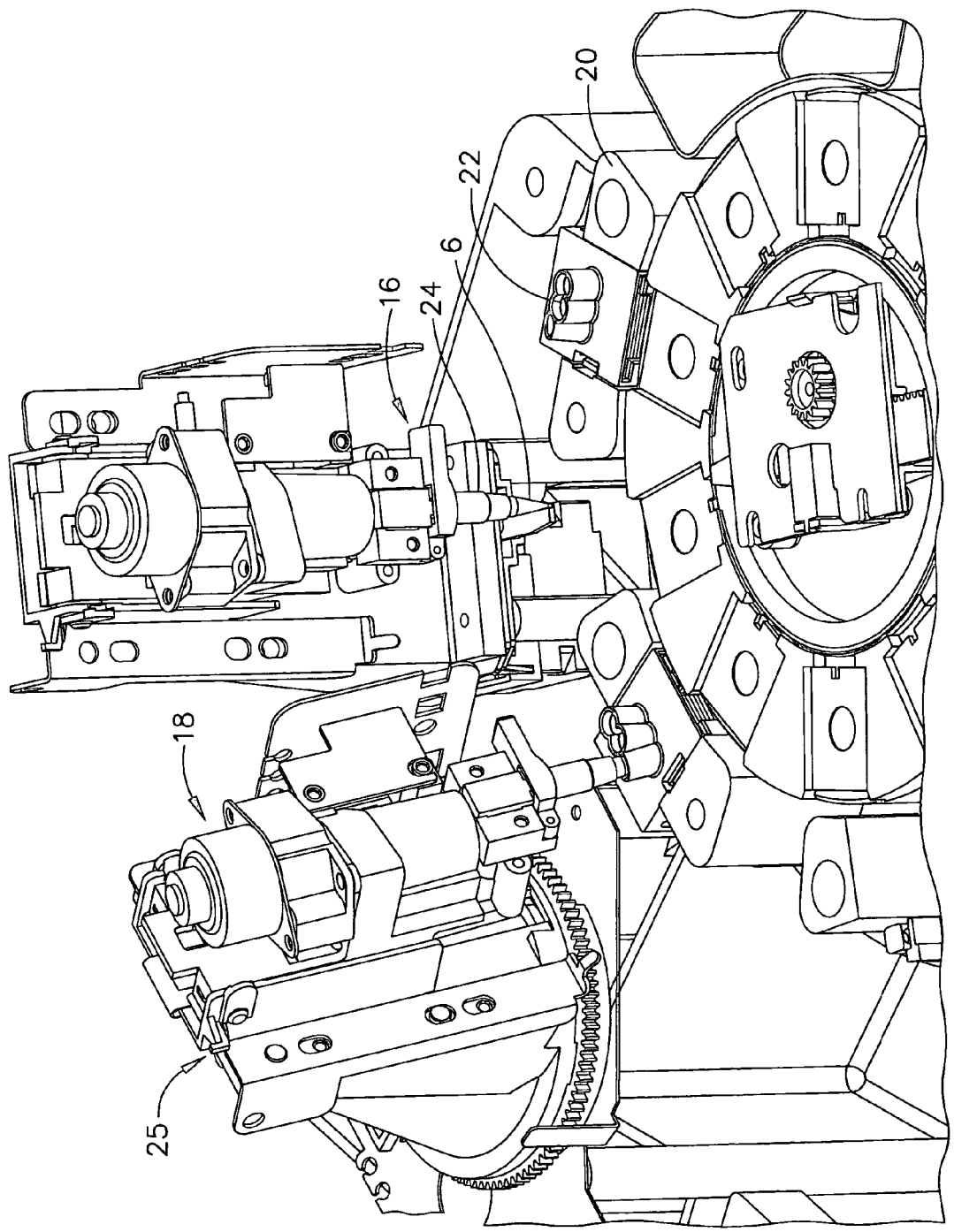
FIG. 5 shows a perspective view of a stationary probe and reference fluid probe according to one aspect of the invention.

In the embodiment shown in the figures, the reagent rotor (1) orients movable fluid supplies (2) concentric to the rotational axis of the reagent rotor (1). The reagent rotor is rotated about its center axis by a motor with a sensor to determine exact positioning. The movable fluid supplies (2) are reusable and are accurately positioned on the reagent rotor using a locating feature (3), which in this embodiment is a peg that inserts into a hole (not shown) on the underside of the movable fluid supply (2) and anti-rotation feature (4), which in this embodiment is a recess that will accept a pin attached to the end of a spring-loaded latch (5). The movable fluid supplies (2) are held in place on the reagent rotor by spring-loaded latches (5) or other means that allow easy loading and unloading of the movable fluid supplies (2) by the user. A single disposable metering or probe tip (6) is placed in a recess on the top of the fluid supply (2) for access by the stationary probe system (16) that includes probe (24, FIG. 5). A patient's sample is placed in a corresponding recess (7) along the same centerline for access by the probe system. A probe guide (8) for metering registration is located on the top of, and in this instance integral with, the holder or cartridge (23) (in this case for test slides) to allow for accurate positioning of the probe tip (6, as shown in FIG. 5) during sample dispense onto the slides in the cartridge or holder. The probe guide includes cover (9) and one or more holes (22). The reagent rotor will also accept a variety of different cartridges (23) that expand the functionality of the system at the discretion of the user. These may include diluent cartridges for performing sample dilutions, immuno rate wash cartridge for performing a wash step prior to final reading of immuno rate chemistries among other cartridge formats that are possible. A waste collection cartridge (10) is also positioned on the reagent rotor and is positioned to automatically collect used metering tips and slides after testing is complete.

As shown in FIG. 2, test slides (11) are loaded into the cartridge (23) prior to processing on the analyzer. The cartridge is capable of accepting a predetermined panel of test slides as well as individual test slides. The test slides (11) are registered up against the inside top surface of the test cartridge directly under the metering registration features by a spring-loaded plunger (12, FIG. 1) mounted to the reagent rotor.

Figure 3:
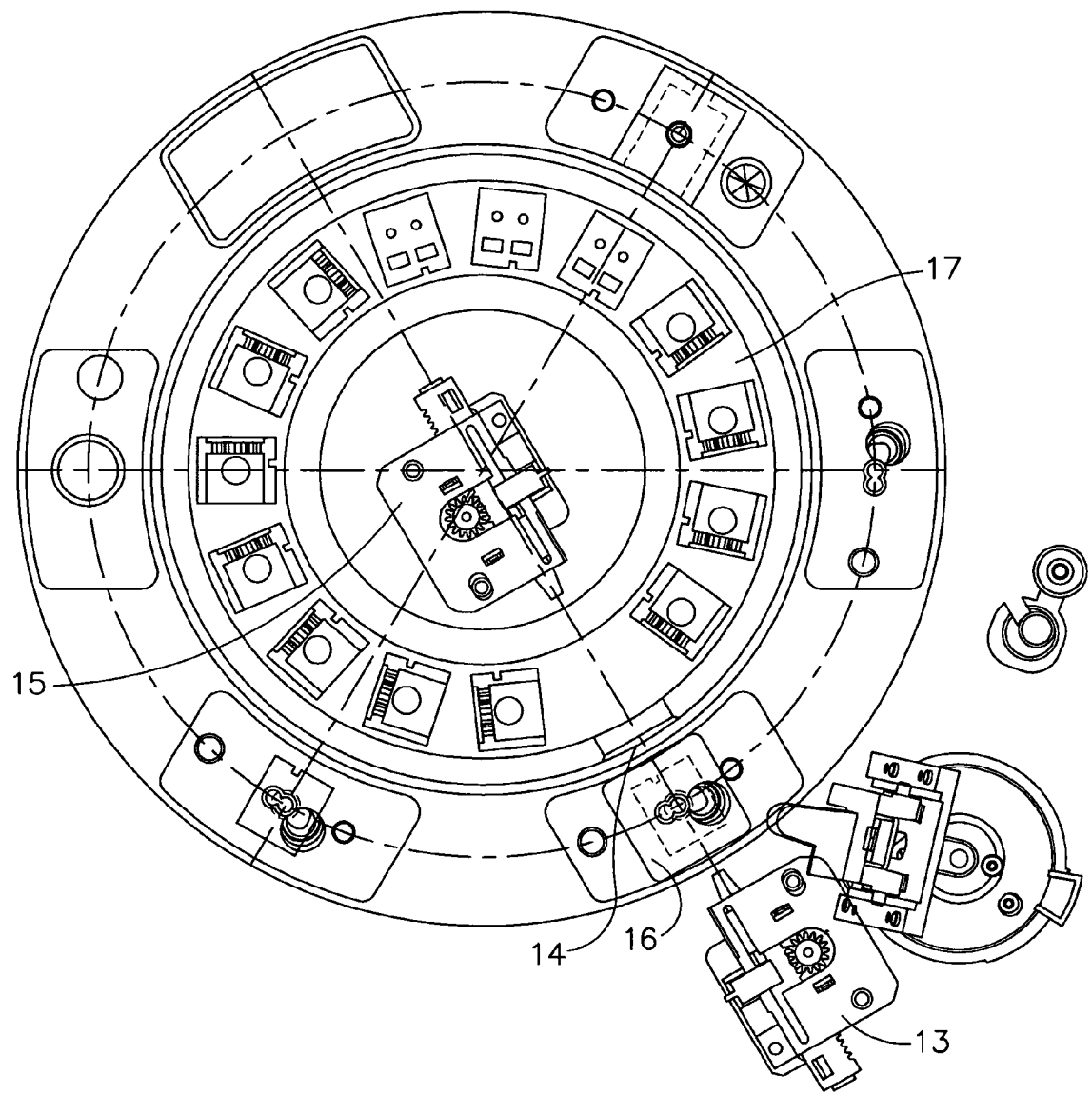
FIG. 3 shows a plan view of a desktop analyzer with the stationary fluid probe according to one embodiment of the present invention.

As shown in FIG. 3, the reagent rotor (1) is automatically positioned to intersect the various components on the slide cartridge with the fixed location of the metering pump. The reagent rotor is able to move clockwise and/or counterclockwise to position the cartridges at the metering station for sample dispense and slide positioning. The reagent rotor first positions the cartridge (23) containing the test slides in front of the slide dispense mechanism (13) that will move the slide to a fixed barcode reader positioned (14) between the reagent rotor and incubator rotor. The barcode reader reads the unique slide barcode to identify the chemistry type to be tested. A slide insert mechanism (15) reinserts the slide into the test cartridge for processing. The reagent rotor then positions the test cartridge to allow the stationary probe system (16) including probe (24) having tip (6) to access the disposable metering tip (6) followed by sample aspiration from the sample container then sample dispense on the top slide in the test cartridge. After sample dispensing, the top slide is transferred into the concentric test element incubator rotor (17) by the slide dispense mechanism for incubation. The incubator rotor (17) is concentric to the reagent rotor and is rotated about its center axis by a motor with a sensor to determine exact positioning. A reflectometer, or spectrometer (not shown) is located below the incubator rotor and is used to measure the slide color change specific to each assay. Immuno rate (IR) chemistries require a wash step prior to final measurement. These slides are inserted into an IR wash cartridge that contains a reusable plastic wash tip and wash fluid supply. The reagent rotor positions the IR wash cartridge at the stationary probe system (16) to perform the necessary wash operation. The IR slide is reinserted into the slide incubator after washing for final measurement.

Figure 4:
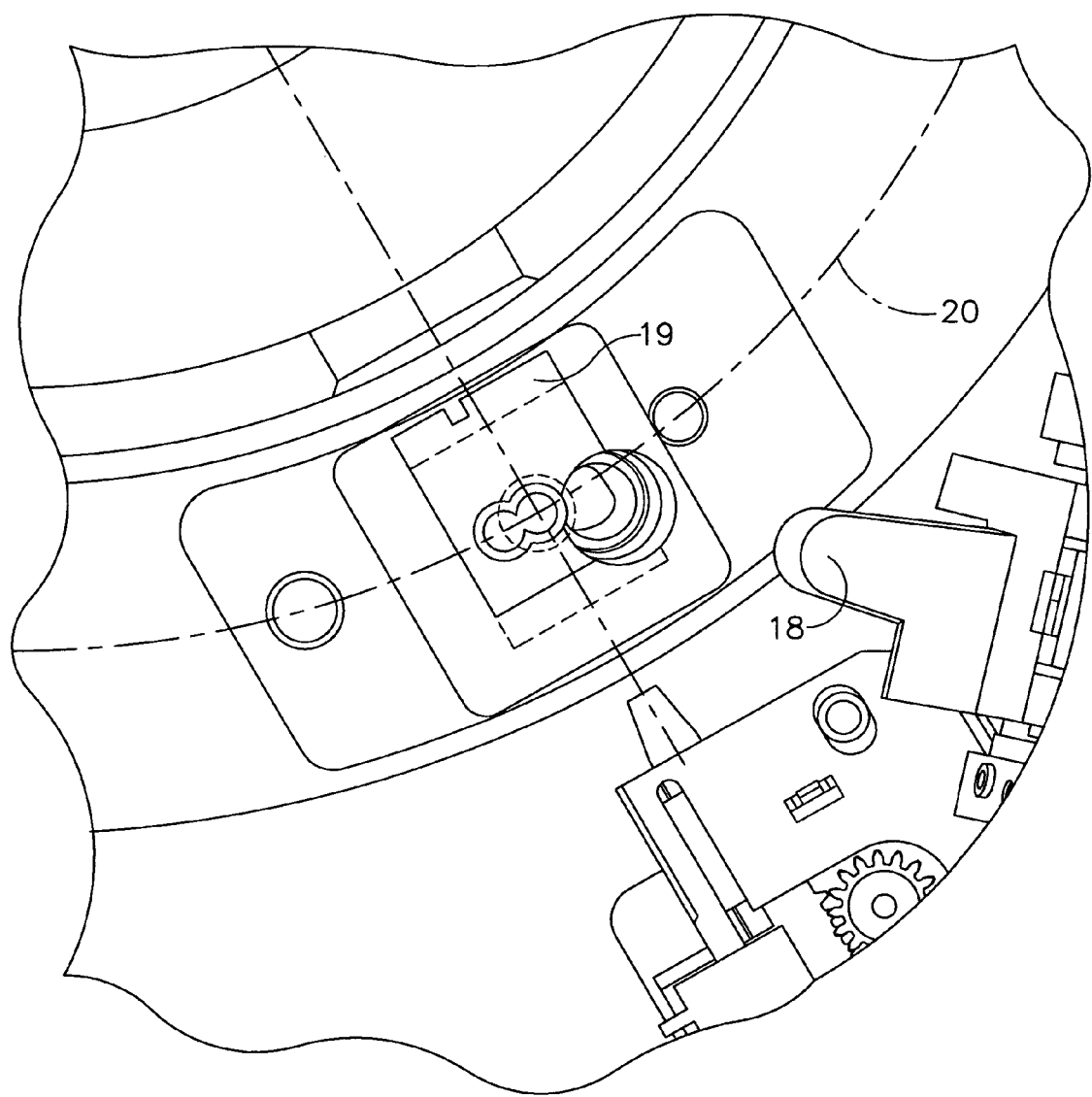
FIG. 4 shows an expanded view of the registration of the stationary fluid probe with the probe guide according to one embodiment of the present invention.

FIGS. 4 and 5 more closely show an embodiment that uses an additional probe. In this instance, additional probe (18) is a dispensing nozzle that dispenses an electrolyte reference fluid for electrolyte chemistry or potentiometric slides (PM Slides). As shown in FIG. 4, the PM slides are processed in a similar manner as the colorimetric (CM) and immuno rate slides. Patient sample and electrolyte reference fluid are dispensed simultaneously on the PM slides (19) while in the test cartridge. In order to eliminate the need for an additional pump movement to intersect the PM slide sample spot, the slide insert mechanism will offset the PM slide slightly. That is, after barcode reading, the slide insert mechanism (15) will push the slide back into the cartridge to a point that aligns the slide underneath the probe guides (22) for metering. The center probe guide is used for sample dispense for CM and immuno rate slides. The left and right probe guides are for sample and reference fluid dispense to PM slides. This allows the CM and PM slides to intersect the common reagent rotor centerline (20). The common reagent centerline (20) allows the stationary probe system (16) and hence the probe (24) to be in a fixed location while all discrete functional interactions with the reagent rotor (1) are accomplished as the reagent rotor is automatically positioned with the fixed location. As shown in FIG. 5, the additional probe (18) may have an additional degree of freedom of movement around pivot (25) to allow access to the reservoir of reference fluid (26).

In a preferred embodiment, the methods described above can be implemented by a computer program interfacing with a computer, that can include a computer usable medium having computer readable program code configured to conduct the methods.

In another preferred embodiment, the analyzer is a veterinary analyzer that includes a T4 assay.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

We claim:

1. An analyzer comprising:
   a stationary probe movable only along a single axis capable of dispensing or aspirating a liquid; and
   a first reagent rotor for holding and moving with respect to the stationary probe a test element and at least one of a movable liquid supply and a probe tip dispenser;
   a second incubator rotor arranged concentrically within the first rotor and adapted to receive the test element from the first rotor and to incubate a sample disposed in the second rotor; and
   a waste collection container located on the first rotor.

2. An analyzer as claimed in claim 1, wherein the probe comprises an aspirating and/or dispensing nozzle.

3. An analyzer as claimed in claim 1, further comprising:
   the movable liquid supply; and
   a test element holder.

4. An analyzer as claimed in claim 3, wherein the test element holder is located within the movable liquid supply.

5. An analyzer as claimed in claim 4, wherein the movable liquid supply comprises a liquid supply section and a probe tip holder.

6. An analyzer as claimed in claim 3, wherein the test element holder comprises a plurality of test holders.

7. An analyzer as claimed in claim 6, wherein at least one of the test element holders contains different test elements than the test elements of other test element holders.

8. An analyzer as claimed in claim 7, wherein the different test elements are potentiometric test elements and the test elements of the other test element holders are colorimetric test elements.

9. An analyzer as claimed in claim 4, wherein the movable liquid supply further comprises a recess for the test element holder.

10. An analyzer as claimed in claim 1, wherein the liquid comprises one or more of a liquid sample, a liquid reagent or a wash liquid.

11. An analyzer as claimed in claim 10, further comprising a liquid reagent source and a liquid sample source, and optionally a wash liquid source.

12. An analyzer as claimed in claim 1, further comprising an additional probe.

13. An analyzer as claimed in claim 1, wherein the additional probe is a dispensing nozzle for dispensing a reference liquid for a potentiometric analysis.

14. An analyzer as claimed in claim 1, further comprising a test element holder that comprises:
   a body portion for holding the movable test element; and
   a guide adapted to receive a probe to position the probe in a desired registration with a test element.

15. An analyzer as claimed in claim 14, wherein the test holder further comprises a cover disposed over at least a portion of the body portion and test element and the guide comprises at least one opening in said cover.

16. An automated analyzer as claimed in claim 5, wherein the liquid supply section includes a recess and the probe tip holder includes a recess.

17. An automated analyzer as claimed in claim 5, wherein the liquid supply section and probe tip holder are integral.

18. An automated analyzer as claimed in claim 5, wherein the movable liquid supply further comprises a recess for the test element holder.

19. An automated analyzer as claimed in claim 16, wherein the liquid movable liquid supply further comprises a recess for the test element holder.

20. An automated analyzer as claimed in claim 19, wherein the recess is disposed between the liquid supply section and the probe tip holder.

21. An analyzer according to claim 1, wherein the analyzer is a desktop analyzer.

22. A desktop analyzer comprising:
   a first rotor for holding a test element, and at least one of a sample reservoir for a sample to be analyzed, a wash reservoir, and a probe tip dispenser;
   an incubator located on a second rotor arranged concentrically within the first rotor and adapted to receive the test element from the first rotor and to incubate a sample disposed in the second rotor;
   a measurement device arranged to analyze a sample located in the second rotor; and
   a waste collection container located on the first rotor.

* * * * *